(12) United States Patent
Simmonds

(10) Patent No.: US 6,275,031 B1
(45) Date of Patent: Aug. 14, 2001

(54) METHOD AND APPARATUS FOR MAKING QUANTITATIVE MEASUREMENTS OF LOCALIZED ACCUMULATIONS OF MAGNETIC PARTICLES

(75) Inventor: Michael Bancroft Simmonds, Del Mar, CA (US)

(73) Assignee: Quantum Design, Inc., San Diego, CA (US)

(*) Notice: Subject to any disclaimer, the term of this patent is extended or adjusted under 35 U.S.C. 154(b) by 0 days.

(21) Appl. No.: 09/576,103

(22) Filed: May 22, 2000

Related U.S. Application Data

(63) Continuation of application No. 08/975,569, filed on Nov. 21, 1997, and a continuation of application No. PCT/US98/17815, filed on Aug. 27, 1998.

(51) Int. Cl.[7] .......................... G01N 27/72; G01N 27/74
(52) U.S. Cl. .................. 324/239; 324/204; 324/226; 324/71.4; 422/68.1; 436/526
(58) Field of Search .................. 324/201, 237, 324/225, 204, 226, 71.1, 71.4, 232, 233, 234, 236, 243, 239; 422/68.1; 436/526

(56) References Cited

U.S. PATENT DOCUMENTS

| | | | |
|---|---|---|---|
| 4,537,861 | 8/1985 | Elings et al. | 436/518 |
| 4,810,963 | 3/1989 | Blake-Coleman et al. | 324/204 |
| 4,876,504 | 10/1989 | Blake et al. | 324/204 |
| 4,913,883 | 4/1990 | Imai et al. | 422/82.01 |
| 5,001,424 | 3/1991 | Kellett et al. | 324/204 |
| 5,034,689 | 7/1991 | Inoue et al. | 324/225 |
| 5,158,895 | 10/1992 | Ashihara et al. | 436/526 |
| 5,290,708 | 3/1994 | Ashihara et al. | 436/526 |
| 5,318,914 | 6/1994 | Matte et al. | 436/526 |
| 5,445,970 | 8/1995 | Rohr | 436/526 |
| 5,445,971 | 8/1995 | Rohr | 436/526 |
| 5,482,839 | 1/1996 | Ashihara et al. | 435/7.9 |
| 5,486,457 | 1/1996 | Butler et al. | 435/7.2 |
| 5,558,839 | 9/1996 | Matte et al. | 422/101 |

FOREIGN PATENT DOCUMENTS

| | | | |
|---|---|---|---|
| 0625708 | 11/1994 | (EP) | G01N/33/536 |
| 63-90765 | 4/1988 | (JP) | G01N/33/553 |
| WO 96/10644 | 4/1996 | (WO) | C12P/19/34 |

OTHER PUBLICATIONS

D. R. Baselt et al., A Biosensor Based on Force Microscope Technology, Naval Research Laboratory, J. Vac. Science Tech. B., vol. 14, No. 2 (5 pp) (Apr. 1996).

*Primary Examiner*—Jay Patidar
(74) *Attorney, Agent, or Firm*—Baker & Maxham

(57) ABSTRACT

Apparatus for quantitatively measuring groups of magnetic particles. The particles are complexed with substances to be determined and are excited in a magnetic field. The magnetic particles are thereby caused to oscillate at the excitation frequency in the manner of a dipole to create their own fields. These fields are inductively coupled to sensing coils fabricated in a gradiometer configuration. The output signals from the sensing coils are appropriately amplified and processed to provide useful output indications.

23 Claims, 4 Drawing Sheets

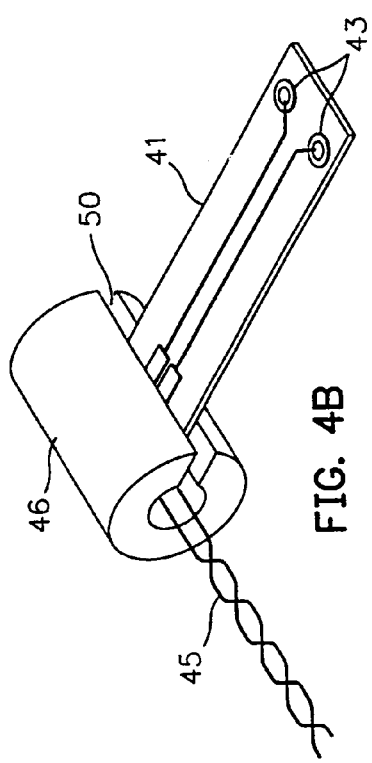
FIG. 4A
FIG. 4B
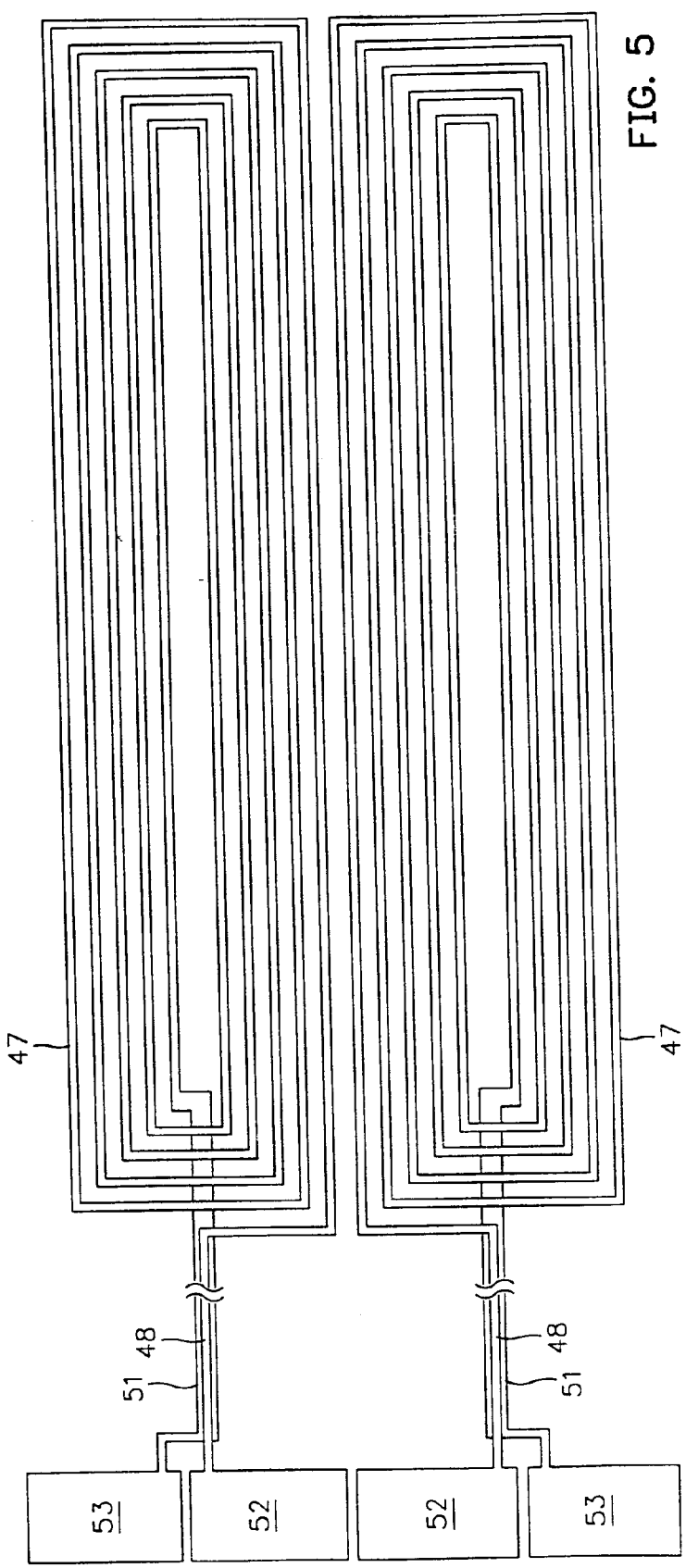
FIG. 5

METHOD AND APPARATUS FOR MAKING QUANTITATIVE MEASUREMENTS OF LOCALIZED ACCUMULATIONS OF MAGNETIC PARTICLES

This application is a continuation of copending application(s) application Ser. No. 08/975,569 filed on Nov. 21, 1997 and International Application PCT/US98/17815 filed on Aug. 27, 1998 and which designated the U.S.

TECHNICAL FIELD

This invention relates generally to sensing the presence of magnetic particles, and more particularly to quantitatively measuring accumulations of such particles by means of AC magnetic excitation and inductive sensing of the amplitude of the resulting oscillation of the magnetic moment of the particles at the excitation frequency.

BACKGROUND ART

Much attention has been given to techniques for determining the presence, and possibly the level of concentration, of minute particles in a larger mixture or solution in which the particles reside. It is desirable in certain circumstances to measure very low concentrations of certain organic compounds. In medicine, for example, it is very useful to determine the concentration of a given kind of molecule, usually in solution, which either exists naturally in physiological fluids (for example, blood or urine) or which has been introduced into the living system (for example, drugs or contaminants).

One broad approach used to detect the presence of a particular compound of interest, referred to as the analyte, is the immunoassay, in which detection of a given molecular species, referred to generally as the ligand, is accomplished through the use of a second molecular species, often called the antiligand, or the receptor, which specifically binds to the first compound of interest. The presence of the ligand of interest is detected by measuring, or inferring, either directly or indirectly, the extent of binding of ligand to antiligand.

A good discussion of several detection and measurement methods appears in U.S. Pat. No. 4,537,861 (Elings et al.). That patent is directed to several ways to accomplish homogenous immunoassays in a solution of a binding reaction between a ligand and an antiligand which are typically an antigen and an antibody. The teaching of Elings is to create a spatial pattern formed by a spatial array of separate regions of antiligand material and ligand material dispersed to interact with the spatial array of separate regions of antiligand material for producing a binding reaction between the ligand and the antiligand and in the spatial patterns and with the bound complexes labeled with a particular physical characteristic. After the labeled bound complexes have been accumulated in the spatial patterns, the equipment is scanned to provide the desired immnoassay. The scanner may be based on fluorescence, optical density, light scattering, color and reflectance, among others.

The labeled bound complexes are accumulated on specially prepared surface segments according to Elings, or within an optically transparent conduit or container by applying localized magnetic fields to the solution where the bound complexes incorporate magnetic carrier particles. The magnetic particles have a size range of 0.01 to 50 microns. Once the bound complexes are accumulated magnetically within the solution, the scanning techniques previously described are employed.

Magnetic particles made from magnetite and inert matrix material have long been used in the field of biochemistry. They range in size from a few nanometers up to a few microns in diameter and may contain from 15% to 100% magnetite. They are often described as superparamagnetic particles or, in the larger size range, as beads. The usual methodology is to coat the surface of the particles with some biologically active material which will cause them to bond strongly with specific microscopic objects or particles of interest (proteins, viruses, cells. DNA fragments, for example). The particles then become "handles" by which the objects can be moved or immobilized using a magnetic gradient, usually provided by a strong permanent magnet. The Elings patent is an example of tagging using magnetic particles. Specially constructed fixtures using rare-earth magnets and iron pole pieces are commercially available for this purpose.

Although these magnetic particles have only been used in practice for moving or immobilizing the bound objects, some experimental work has been done on using the particles as tags for detecting the presence of the bound object. This tagging is usually done by radioactive, fluorescent, or phosphorescent molecules which are bound to the objects of interest. A magnetic tag, if detectable in sufficiently small amounts, would be very attractive because the other tagging techniques all have various important weaknesses. Radioactive methods present health and disposal problems. They are also relatively slow. Fluorescent or phosphorescent techniques are limited in their quantitative accuracy and dynamic range because emitted photons may be absorbed by other materials in the sample. See Japanese patent publication 63-90765, published Apr. 21, 1988 (Fujiwara et al.).

Because the signal from a very tiny volume of magnetic particles is exceedingly small, it has been natural that researchers have tried building detectors based on Superconducting Quantum Interference Devices (SQUIDs). SQUID amplifiers are well known to be the most sensitive detectors of magnetic fields in many situations. There are several substantial difficulties with this approach, however. Since the pickup loops of the SQUID must be maintained at cryogenic temperatures, the sample must be cooled to obtain a very close coupling to these loops. This procedure makes the measurements unacceptably tedious. The general complexity of SQUIDS and cryogenic components renders them generally unsuitable for use in an inexpensive desktop instrument. Even a design based on "high Tc" superconductors would not completely overcome these objections, and would introduce several new difficulties. (Fugiwara et al.).

There have been more traditional approaches to detecting and quantifying the magnetic particles. These have involved some form of force magnetometry, in which the sample is placed in a strong magnetic gradient and the resulting force on the sample is measured, typically by monitoring the apparent weight change of the sample as the gradient is changed. An example of this technique is shown in Rohr U.S. Pat. Nos. 5,445,970 and 5,445,971. A more sophisticated technique measures the effect of the particle on the deflection or vibration of a micromachined cantilever. (Baselt et al., A Biosensor based on Force Microscope Technology, Naval Research Lab., J. Vac. Science Tech. B., Vol 14, No.2 (5pp) (Apr. 1996) These approaches are all limited in that they rely on converting an intrinsically magnetic effect into a mechanical response. This response must then be distinguished from a large assortment of other mechanical effects such as vibration, viscosity, and buoyancy.

There would be important applications for an inexpensive, room-temperature, desktop instrument which could directly sense and quantify very small amounts of magnetic particles.

DISCLOSURE OF INVENTION

Broadly speaking, the present invention provides a method and an apparatus for directly sensing and measuring very small accumulations of magnetic particles (for example, magnetite) and consequently, their coupled substances of interest.

The invention consisted essentially of apparatus for employing magnetic particles for quantitative measurement of target particles, the magnetic particles and target particles being combined to form magnetic bound complex samples, said apparatus comprising: a movable substrate on which the samples are deposited in defined patterns; a magnetizer for applying an alternating magnetic field to the samples; magnetic field sensing elements having output signal conductors; apparatus for moving said samples into the magnetic field and into operative relationship with said sensing elements which have resultant output signals; a signal processor comprising processor and analyzer elements for converting said output signals from said sensing elements to provide a signal indicative of the quantity of said samples in a pattern; and apparatus for converting said quantity indicating signal to a human useful form.

The magnetic particles or beads are coupled by known methods to target particles, thereby providing magnetic sample elements or magnetic bound complexes. A well-defined pattern of the magnetic sample elements is deposited on a flat substrate. A high-amplitude, high-frequency magnetic field is then applied to excite the particles of magnetite in this sample. This causes the particles to behave as a localized dipole oscillating at the excitation frequency. These fields from the sample are closely coupled to an array of inductive sensing coils which have been fabricated in a gradiometer configuration. This configuration makes the sensing coils mostly insensitive to the large, uniform field which is used to excite the sample. Moreover, the geometry of the coils is designed to match the spatial pattern of the sample so as to provide a large response which varies distinctively with the relative positions of the sample and coils. The voltage induced across the sensing coils is carefully amplified and processed by phase-sensitive detection. An inductive pickup from the drive field itself serves as the reference signal to the phase detector circuit. The output of the phase detector is further filtered and then digitized.

The signal amplitude is modulated by moving the sample with respect to the sense coil array. This allows one to reject signals due solely to imbalance of the coils, non-uniformity of the drive field, cross-talk in the circuitry, or any other source of apparent signal which is not due to the sample itself. The digitized shape of the signal amplitude with respect to sample position is compared to the theoretical response shape using appropriate curve fitting techniques. This provides a very accurate estimate of the magnetic content of the sample in the face of inherent instrument noise and drift.

BRIEF DESCRIPTION OF THE DRAWING

The object, advantages and features of this invention will be more clearly perceived from the following detailed description, when read in conjunction with the accompanying drawing, in which:

FIG. 4A is an enlarged plan view of the substrate holding the sensing coils of FIG. 1;

FIG. 4B is a perspective view of a metal shield for the connection end of the substrate;

FIG. 5 is a greatly enlarged plan view of an alternative embodiment of the sensing coils of the FIG. 1 invention; and FIG. 6 is a signal waveform of the output of the sensing coils as the material to be measured passes by them.

BEST MODE FOR CARRYING OUT THE INVENTION

Figure 1:
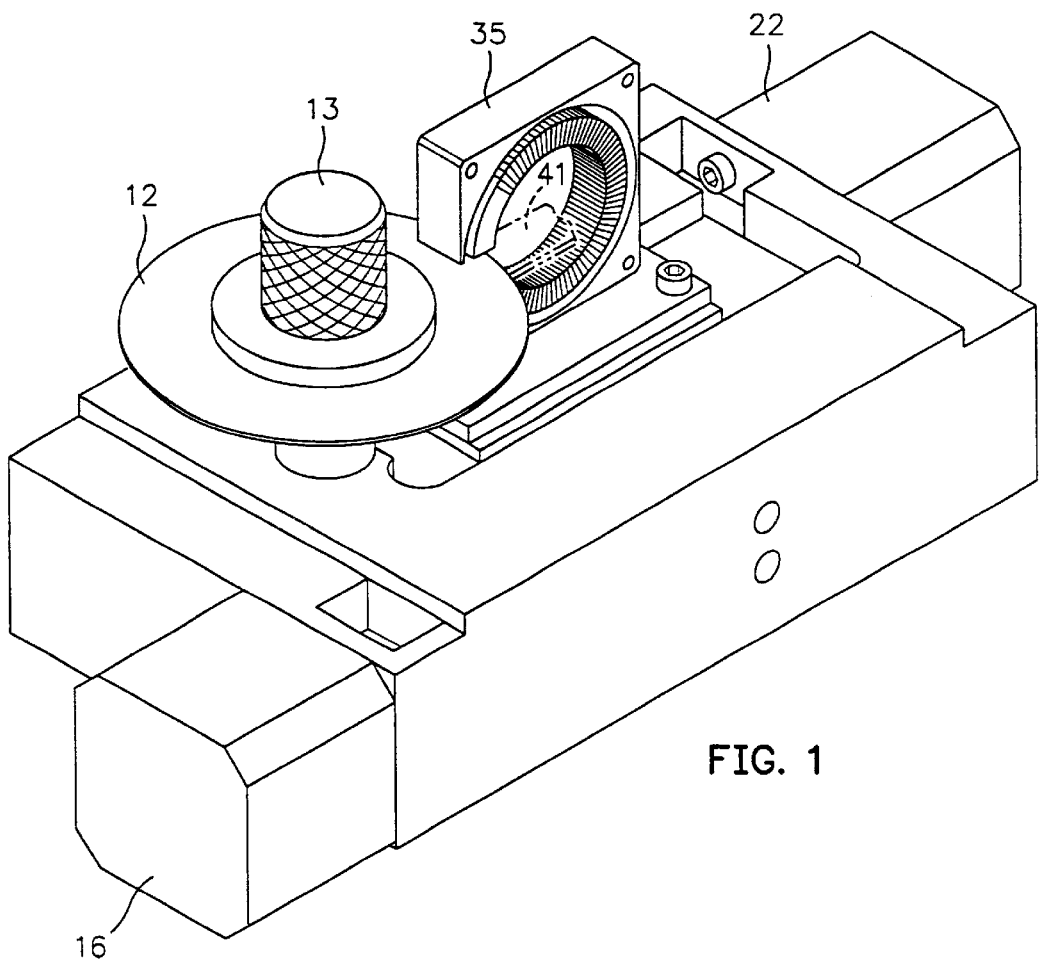
FIG. 1 is a perspective view of a desktop version of the present invention.
Figure 3:
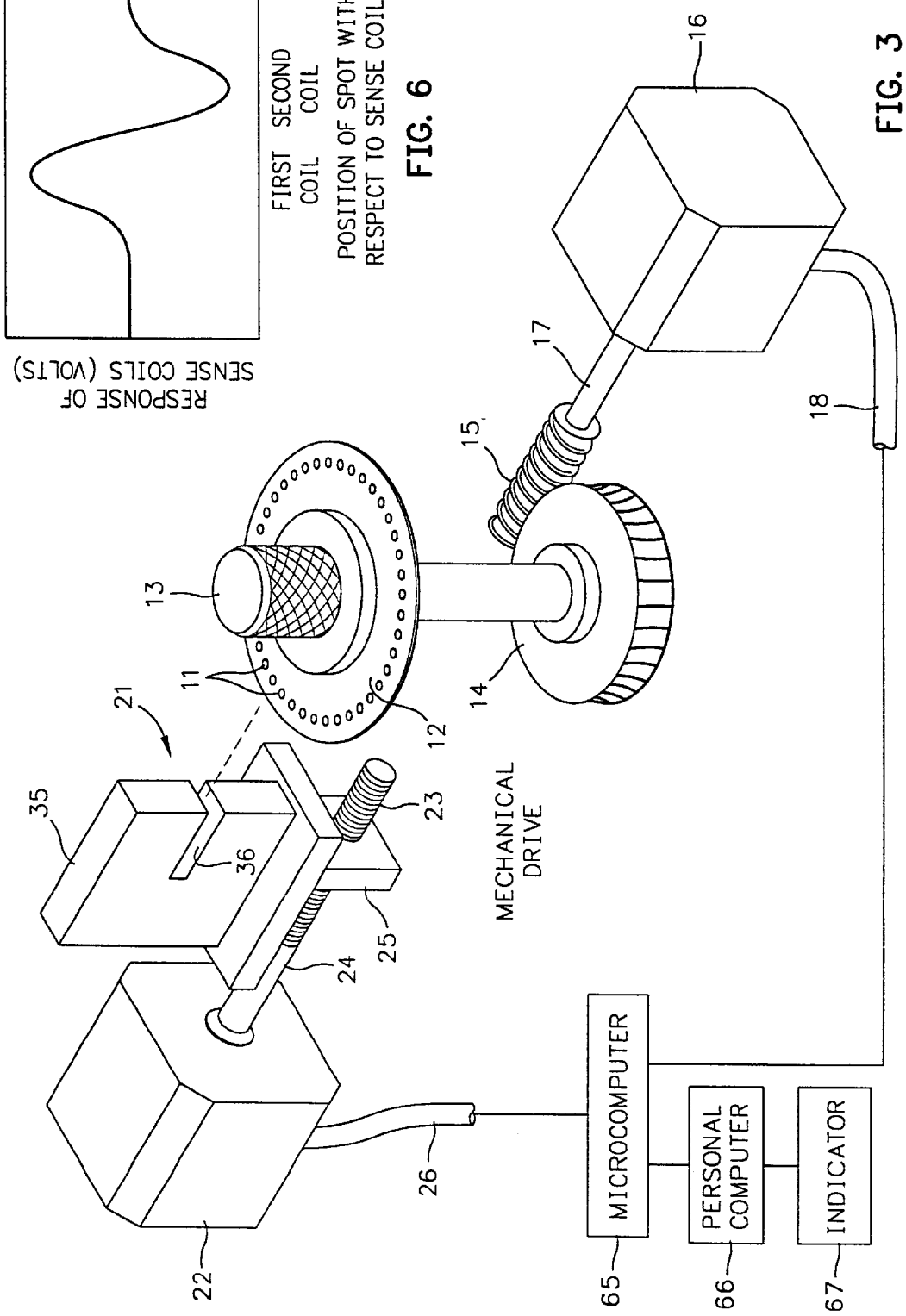
FIG. 3 is a mechanical schematic perspective view of the invention of FIG. 1.

Referring now to the drawing, and more particularly to FIGS. 1 and 3 thereof, there is shown the preferred embodiment of the invention.

I. Reader Module

The reader module comprises several distinct subsystems. These are: a sample motion control having a substrate on which reside the magnetic bound complex samples for measurement and which provides the necessary relative motion within the system; a magnetizer, which applies the excitation signals to the samples; sensing coils which act as the signal pick-up means for the signals generated in the samples; a drive circuit which supplies the drive current to the coils of the magnetizer; an amplifier/phase detector/digitizer which is coupled to the sensing coils to receive and process the output signals therefrom; and a microcomputer chip which provides two-way communication between the external personal computer (PC) and the reader module.

A. Sample Motion Control

Magnetic particles are coupled to target particles by conventional methods to create magnetic bound complex samples. The target particles may include atoms, individual molecules and biological cells, among others. The magnetic bound complex samples are deposited in accumulations of several to several hundred particles at predetermined positions 11 near the perimeter of substrate or disc 12 (FIG. 3). The means by which the bound complexes are formed and by which they are adhered to the pre-defined spots on the disc are well known and employ standard technology. The disc is mounted on axial shaft 13 which extends downwardly to toothed wheel 14. An appropriate rotational device, such as stepper motor 16, has shaft 17 extending therefrom with worm gear member 15 at the distal end thereof. The motor provides controlled rotary motion of disc 12 pursuant to signals applied from PC 66 through wires 18. Of course, wireless coupling between the PC and the system of the invention could be used if desired.

In the preferred embodiment, as presently contemplated, disc 12 is about 47 mm in diameter and about 0.25 mm thick. It may be made of glass, plastic or silicon, for example. Its thickness range, for practical functional purposes, would be about 0.1 mm to about 1.0 mm. In this particular exemplary embodiment, wheel 14, which is connected to disc 12 by shaft 13, is rotated by motor 16 through a 120-tooth worm gear reduction. Of course, rotational drives having different particulars could be employed.

Magnetizer 21 is moved linearly with respect to disc 12 by a rotational device, such as stepper motor 22, having 40 turn-per-circle lead screw 23 on motor shaft 24. Boss 25 is configured with a hole having internal threads to which the spiral lead screw threads are coupled. The control signals are applied from microcomputer 65 to motor 22 through wires 26. Again, the specifics of the rotational drive are set out here as an example only. Other appropriate elements having different characteristics could be used.

B. Magnetizer

Figure 4:
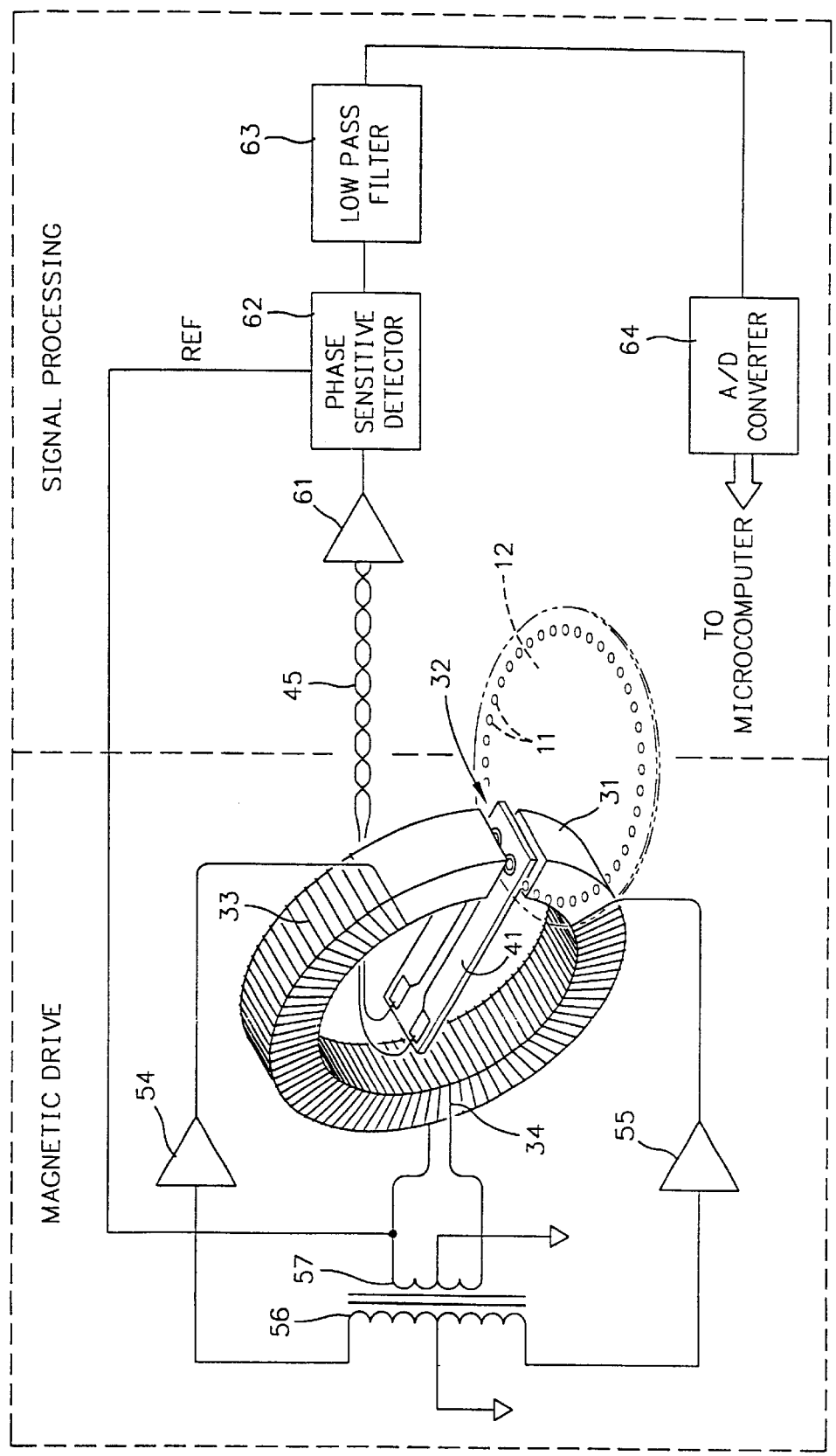
FIG. 4 is an electrical schematic diagram of the invention of FIG. 1.

In the preferred embodiment, ferrite toroid core 31 (FIG. 4), which is about 30 mm in diameter in the particular embodiment being described, is formed with gap 32, which is about 1.5 mm wide. Drive coil 33 is wound as a single layer over about 270° of toroid 31, symmetric with respect to the gap. Feedback loop 34 encircles the toroid body at a location about 180° from (opposite) the gap. Loop 34 may be outside of coil 33 or between coil 33 and the toroid core. It may consist of a few or many turns, as necessary and appropriate for the feedback function. The purpose of the feedback loop is to sense or represent the field in gap 32 and enable the signal processing or output circuit to self correct for such things as temperature drift This is used to enhance precision and is not essential to proper operation of the system. The toroidal magnetizer assembly is mounted in insulative housing 35, which may be formed from a glass fiber material. Housing 35 has a slot 36 corresponding to the position of gap 32 (FIG. 4). This slot/gap is shaped and configured to selectively receive the edge of rotatable disc 12, and provides space for the sensing coil substrate, which is described in detail below.

C. Sensins Coils

Figure 2:
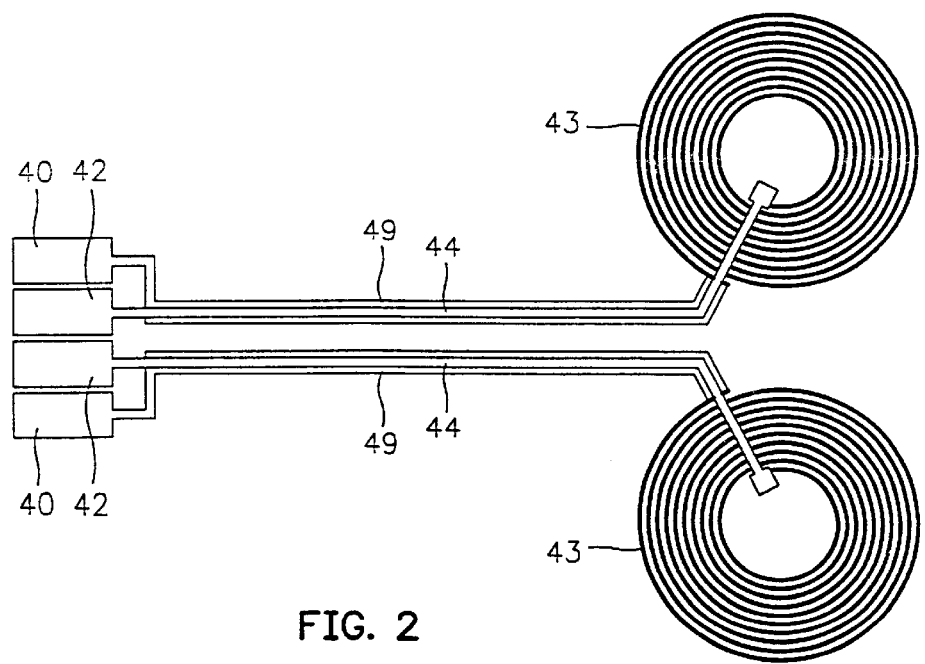
FIG. 2 is a greatly enlarged plan view of an embodiment of the sensing coils of the invention of FIG. 1.

With particular reference now to FIGS. 2, 4 and 4A, insulative substrate 41 is mounted to extend into slot 36 in housing 35 and extends into gap 32. The position of substance 41 with respect to the gap and disc 12 is shown in FIG. 1. Disc 12 is shown in phantom in FIG. 4 in its position with respect to gap 32 and coils 43. Bonding pads 40, 42 are provided at the proximal end and sensing coils 43 are mounted on the substrate adjacent to the distal end thereof. Preferably the substrate is made of sapphire or silicon and the sensing elements are thin film copper coils. Standard thin film fabrication techniques can be used to construct the substrate and sensing coils, where the leads to and from each coil are on two different layers. For example, incoming traces 49 may be laid on the substrate surface by standard photolithographic processing methods, a layer of sputtered quartz may then cover the incoming leads, then coils 43 and output leads 44 are similarly applied and a protective layer of quartz may then be added on top. The usual means for connecting between layers would be used.

The sensing coils, which are connected in series opposition creating a gradiometer configuration, are connected to bonding pads 40, 42 by conductive traces 44, 49, and thence to signal processing circuitry by twisted-pair wires 45. The twisted pair arrangement is employed to assist in reducing stray signal or interference pickup.

In the spiral form shown in FIG. 2, the coil traces would be about 5 microns in width with about a 10-micron pitch between spiral traces. The thickness of the sensing coil traces would normally be about 1 micron. The diameter of each completed coil is about 0.25 mm.

By making substrate 41 relatively long and narrow, bonding pads 40, 42 are relatively far away from the toroid gap, which helps minimize stray pickup in soldered leads 45. Metal shield 46 (FIG. 4B) may be employed around the bonding area to further contribute to reducing stray signal or interference pickup. The connection (proximal) end of the substrate is slid into slot 50 after the wire connections are made. The shield is essentially a short piece of a thick-walled cylinder, typically formed of copper. The shield provides electrical shielding and facilitates mechanical handling, but it is not essential to operation of the system of the invention.

An alternative embodiment of the sensing coils is shown in FIG. 5. The planar configuration of coils 47 is an elongated rectangle. The trace dimensions are about the same as for the FIG. 2 coils and the composite coil width is also about 0.25 mm. The coil length is about 1–2 mm and the coils are connected to bonding pads 52, 53 by means of leads 48, 51.

D. Drive Circuit

The magnetic drive circuit, shown at the left side of FIG. 4, is built around a pair of high-current, high-speed operational amplifiers 54, 55. With the power provided by transformer primary winding 56, the amplifiers can provide in excess of about one ampere of drive current to magnetizing or drive coil 33 at about 200 KHz. This drive circuit is highly balanced to minimize common-mode noise pickup in sensing loops or coils 43, 47.

Small secondary winding 57 coupled to loop 34 around the magnetizing coil provides feedback voltage to operational amplifiers 54, 55, to sustain oscillations at a well regulated amplitude and frequency. This secondary winding 57 also provides an optimum reference signal for the phase-detector circuitry, described below.

E. Amplifier/Phase Detector/Digitizer

A low-noise integrated instrumentation amplifier is the basis for this circuitry, although somewhat better noise performance could be obtained using discrete components. Amplifier 61 is transformer coupled to the sensing coils in order to reduce common-mode noise signals, and to facilitate a convenient way to null out imbalance in the magnetizer and in the sensing coils. The transformer coupling is conventional, is located in amplifier 61, and is not specifically shown in the drawing. Phase sensitive detector 62 is also designed around a special purpose integrated circuit. The output of the phase detector is applied to low-pass filter 63 and is then digitized in A/D converter 64. The converter may be a high resolution, 20 bit sigma-delta converter, for example. This converter chip has excellent hum rejection at both 60 and 50 Hz, which proves to be very helpful in maximizing the sensitivity of the instrument. It is an off-the-shelf item, available from several manufacturers.

F. Microcomputer

Microcomputer 65 includes a microprocessor chip, such as a Motorola HC11, and has a built-in port which supports two-way serial communication to PC 66 by plugging into the serial port of the PC. It also has specialized parts for communication with serial A/D converter 64 and stepper motors 16 and 22. A simple command language programmed directly into microcomputer 65 allows the PC to send commands and receive responses and data.

G. Human Interface

The PC provides the operational command for the system of the invention. It runs the system through an RS232 interface, for example, from the microcomputer.

II. Operation of the System

In a relatively straightforward and known manner, a well defined dot or pattern of the magnetic particle complexes comprising the samples is deposited on disc 12 at one or more locations 11 near the periphery thereof. Pursuant to control signals from the PC, stepper motor 22 is energized to rotate lead screw 23 to move the magnetizer assembly toward sample disc 12. When a sample position 11 near the peripheral edge of disc 12 is aligned with sensing coils 43, 47 in the middle of toroidal gap 32, stepper motor 22 stops and a high amplitude (1 ampere, for example), high frequency (200 KHz) signal is applied to toroidal drive coil 33. A signal from PC 66 then energizes stepper motor 16 to rotate the disc and thereby move the sample dot past the sensing coils. The high amplitude, high frequency magnetic field in gap 32, thereby excites the magnetic particles of the sample in the gap. It is intended to drive the toroid to saturation, resulting in the field in the gap being at about 1000 Oersted. The particles then oscillate magnetically at the excitation frequency, behaving as a localized dipole. Given the close physical proximity of the magnetic particles to the sensing coil, the magnetic fields from the sample are closely coupled to the gradiometer configured sensing coils. Because of the gradiometer configuration of the sensing coils, the output of the sensing coils due to the large, uniform excitation field is substantially null or zero. In order to obtain the largest possible response, the geometry of the sensing coils is configured to match the spatial pattern of the samples. That is, the sample pattern dots are no larger than about 0.25 mm across. The response signal varies distinctively with the relative position of the sample and the coils.

The signal from the sensing coils in the presence of the drive field and in the absence of a sample serves as the reference signal to the signal processing portion of the invention. As the sample moves past one sensing coil and then the other the phase of their coil output signal reverses by 180° as shown in FIG. 6, thereby providing a very powerful detection technique. The induced voltage is amplified by amplifier 61 and processed by phase detector 62. That signal is filtered and digitized and passed to the PC through microcomputer 65 to provide the output signals to the PC. Indicator 67 may be any type of useable device to provide information to the system operator. It could be a visual indicator, conveying information numerically or graphically, or it could be some type of lighting system, or it could be an audible indicator, or any combination of these or other possible indications.

The output signal amplitude is modulated by moving the sample with respect to the array of the sensing coils. This permits rejection of signals due solely to system and external inputs and not due to the sample itself. The digitized shape of the signal amplitude with respect to sample position is compared to the theoretical response shape stored in PC 66 using appropriate conventional curve fitting techniques. The result of this operation is a very accurate estimate of the magnetic content of the sample to the exclusion of inherent instrument noise and drift.

While the preferred embodiment of the invention has been presented above, some alternatives should be mentioned. Two sensor coil shapes have been shown but there are likely several other viable configurations. The magnetizer is shown as moving with respect to the sample disc, but the disc and coupled stepper motor could be configured to move with respect to the magnetic drive assembly if desired. The toroid core is shown with a rectangular cross section but other shapes are feasible. As to the number of sample particles in a dot 11 on disc 12, by way of example, a 0.25 mm dot of sample elements could contain about 10 five-micron size magnetic particles, or about 1200 one-micron size particles.

In view of the above description it is possible that modifications and improvements may occur to those skilled in the applicable technical field which are within the spirit and scope of the accompanying claims.

What is claimed is:

1. Apparatus for making quantitative measurements of target analyte formed in complex samples comprised of magnetic particles of known size and magnetic characteristics bound to the target analyte, said apparatus comprising:
    a movable substrate in which the samples are deposited in defined patterns;
    magnetic field sensing elements having output signal conductors;
    apparatus for moving said samples into the magnetic field and into operative relationship with said sensing elements which have resultant output signals; and
    a signal processor for converting said output signals from said sensing elements to provide a signal indicative of the quantity of said samples in a pattern.

2. The apparatus of claim 1, wherein said sensing elements are inductive sensing coils.

3. The apparatus of claim 2, wherein said sensing elements are two spaced said sensing coils.

4. The apparatus of claim 3, wherein said sensing coils are connected in a gradiometer configuration.

5. The apparatus of claim 3, wherein said sensing coils are circular spirals.

6. The apparatus of claim 3, wherein said sensing coils are rectangular in shape.

7. The apparatus of claim 1, wherein said moving apparatus provides two dimensional relative motion between said samples and said magnetic field applying means.

8. The apparatus of claim 7, wherein said moving apparatus comprises:
    a motor and screw arrangement for moving the magnetic field generating means linearly with respect to said movable substrate; and
    a motor arrangement for moving said movable substrate and samples past the magnetic field generating means in a predetermined manner.

9. The apparatus of claim 8, wherein:
    said movable substrate is a disc shaped and configured to receive a plurality of patterns of samples; and
    said motor is a stepper motor adapted to rotate said disc in accordance with signals from said signal processor.

10. The apparatus of claim 1, wherein said magnetic field generating means comprises:
    a toroid core having a gap in one side;
    a drive coil wound around said core and leaving said gap clear; and
    means for applying AC power to said drive coil.

11. The apparatus of claim 10, and further comprising a feedback loop coupled to said core and drive coil, the output of said feedback loop being connected to said signal processor to enable said signal processor to self correct for external influences.

12. The apparatus of claim 10, wherein said sensing elements are mounted on a sensor substrate in fixed relationship with and extending, into said gap.

13. The apparatus of claim 12, wherein said sensing, elements are two spaced sensing coils mounted on said sensor substrate and connected in a gradiometer configuration, said sensing coils being positioned in said gap.

14. The apparatus of claim 13, wherein said sensor substrate is elongated and has on its proximal end bonding pads to which are connected conductors for input to and output signals from said sensing coils which are mounted on the distal end of said sensor substrate, said sensor substrate further comprising a conductive shield around said bonding pads and said proximal end of said sensor substrate to reduce stray signal and interference pickup.

15. The apparatus of claim 1, wherein said signal processor comprises:
    an amplifier coupled to the output of said sensing elements;
    a phase sensitive detector connected to said amplifier to condition the output signals;
    an analog to digital converter to convert the output signals to digital form; and
    computation means for receiving said digitized signals and converting them to human useful form and to provide control signals to said apparatus.

16. A method for quantitatively measuring target analyte coupled to magnetic particles to form magnetic bound complex samples, said particles having magnetic moments and magnetic fields associated with said moments, said method comprising:

applying at least one sample pattern in a predetermined configuration on a substrate;

creating a time varying magnetic field in a predefined location;

moving the sample pattern through the magnetic field in a predefined manner to excite the magnetic particles in the pattern and cause a change in the magnetic moments therein;

sensing the fields associated with the magnetic moments of the particles; and creating a signal representative of the quantity of magnetic particles present.

17. The method recited in claim 16, wherein said sensing step is accomplished by a pair of sensing coils connected in a gradiometer configuration.

18. The method recited in claim 16, wherein the substrate is rotatable disc.

19. The method recited in claim 16, wherein the magnetic field is created in a gap in a toroidal core having a drive coil wound therearound.

20. The method recited in claim 19, and comprising the further steps of:

applying groups of sample patterns spaced around at least a portion of the periphery of the disc;

moving the disc periphery into the gap in the toroidal core; and rotating the disc so that the sample patterns pass through the gap.

21. The method recited in claim 16, wherein the magnetic field is created on a toroidal core having a drive coil wound therearound and the creating step is accomplished by means of a signal processor, said method comprising the further steps of:

applying an AC drive signal to a drive coil to create the magnetic field;

feeding back a signal representative of the AC drive signal in the drive coil to the signal processor; and correcting errors in the signal processor resulting from external influences by using the feedback signal.

22. Apparatus for making quantitative measurements of target analyte, said apparatus comprising:

a movable substrate configured to receive samples including said target analyte in defined patterns thereon, said samples being comprised of magnetic particles of known size and magnetic characteristics bound to the target analyte to form magnetic bound complex samples;

a magnetizer for generating a time varying magnetic field;

magnetic field sensing elements having output signal conductors;

apparatus for moving said samples into the magnetic field and into operative relationship with said sensing elements which have resultant output signals; and a signal processor for converting said output signals from said sensing elements to provide a signal indicative of the quantity of said analyte in a pattern.

23. A method for quantitatively measuring target analyte, said method comprising:

applying at least one sample pattern in a predetermined configuration on a substrate, the sample pattern being comprised of magnetic particles of known size and magnetic characteristics coupled to the target analyte to form magnetic bound complex samples, said particles having magnetic moments and magnetic fields associated with said moments;

applying a time varying magnetic field in a predefined location;

moving the sample pattern through the applied magnetic field in a predefined manner to excite the magnetic particles in the pattern and cause a change in the magnetic moments therein;

sensing the fields associated with the magnetic moments of the particles; and creating a signal representative of the quantity of magnetic particles present.

* * * * *